(12) United States Patent
Bergersen

(10) Patent No.: US 8,870,566 B2
(45) Date of Patent: Oct. 28, 2014

(54) ORTHODONTIC APPLIANCE, A SYSTEM AND A METHOD FOR AUTOMATICALLY STRAIGHTENING TEETH

(75) Inventor: Earl O. Bergersen, Dorado, PR (US)

(73) Assignee: Ortho-Tain, Inc., Dorado, PR (US)

( * ) Notice: Subject to any disclaimer, the term of this patent is extended or adjusted under 35 U.S.C. 154(b) by 1942 days.

(21) Appl. No.: 10/447,099

(22) Filed: May 28, 2003

(65) Prior Publication Data
US 2003/0224312 A1    Dec. 4, 2003

Related U.S. Application Data

(60) Provisional application No. 60/383,908, filed on May 28, 2002.

(51) Int. Cl.
| A61C 3/00 | (2006.01) |
| A61C 7/08 | (2006.01) |
| A61C 7/00 | (2006.01) |
| A61C 13/00 | (2006.01) |

(52) U.S. Cl.
CPC . *A61C 7/08* (2013.01); *A61C 7/002* (2013.01); *A61C 13/0013* (2013.01)
USPC .......................................................... 433/6

(58) Field of Classification Search
USPC ................................. 433/6, 24; 128/861–862
See application file for complete search history.

(56) References Cited

U.S. PATENT DOCUMENTS

| 3,510,946 | A | * | 5/1970 | Kesling .............................. 433/6 |
| 3,724,075 | A | | 4/1973 | Kesling |
| 3,837,081 | A | | 9/1974 | Kesling |
| 3,898,736 | A | * | 8/1975 | Bergersen ......................... 433/6 |
| 4,073,061 | A | | 2/1978 | Bergersen |
| 4,105,032 | A | | 8/1978 | Blomstedt |
| 4,139,944 | A | * | 2/1979 | Bergersen ......................... 433/6 |
| 4,370,129 | A | | 1/1983 | Huge |
| 4,371,336 | A | | 2/1983 | Hilleman |
| 4,396,373 | A | | 8/1983 | Dellinger |
| 4,419,992 | A | * | 12/1983 | Chorbajian .................. 128/862 |
| 4,568,280 | A | | 2/1986 | Ahlin |

(Continued)

FOREIGN PATENT DOCUMENTS

WO    WO 98/58596    * 12/1998 ............... A61C 7/00

OTHER PUBLICATIONS

Kesling, "The Philosphy of the Tooth Positioning Appliance", American Journal of Orthodontics and Oral Surgery, vol. 31, No. 6, Jun. 1945. pp. 297-302.*

(Continued)

*Primary Examiner* — Heidi M Eide
(74) *Attorney, Agent, or Firm* — Patents + TMS, P.C.

(57) ABSTRACT

An apparatus, a system and a method provide automatic tooth straightening. An appliance may be placed on teeth to straighten teeth. The appliance or series of appliances may be made to fit a particular patient. The appliance may fit onto the teeth that do not require straightening using a section that may be made from relatively stiff material. The erupted teeth that require straightening may be straightened with a softer more resilient material. The unerupted teeth may be guided into the mouth by another portion of the appliance that is preformed with predicted sizes and shapes of teeth determined from sizes of other erupted adult teeth and shapes from anatomical standards. A hard stiffer inner shell and/or a stiffer isthmus having a softer material is overlayed to directly contact the teeth.

27 Claims, 6 Drawing Sheets

(56) References Cited

U.S. PATENT DOCUMENTS

| | | | |
|---|---|---|---|
| 4,591,341 A | 5/1986 | Andrews | |
| 4,784,605 A | 11/1988 | Bergersen | |
| 4,793,803 A * | 12/1988 | Martz | 433/6 |
| 4,799,884 A | 1/1989 | Bergersen | 433/6 |
| 4,830,612 A | 5/1989 | Bergersen | |
| 4,898,535 A | 2/1990 | Bergersen | |
| 4,919,612 A | 4/1990 | Bergersen | |
| 4,983,334 A | 1/1991 | Adell | |
| 4,986,751 A | 1/1991 | Bergersen | |
| 5,028,231 A | 7/1991 | Hall | |
| 5,037,294 A * | 8/1991 | Bergersen | 433/6 |
| 5,037,295 A | 8/1991 | Bergersen | |
| 5,042,506 A | 8/1991 | Liberati | |
| D323,215 S | 1/1992 | Bergersen | |
| 5,203,695 A * | 4/1993 | Bergersen | 433/6 |
| 5,328,362 A | 7/1994 | Watson et al. | |
| 5,334,218 A | 8/1994 | Johnson | |
| 5,338,190 A | 8/1994 | Tregillis | |
| 5,645,420 A | 7/1997 | Bergersen | |
| 5,683,244 A | 11/1997 | Truax | |
| 5,779,470 A | 7/1998 | Kussick | |
| 5,814,074 A | 9/1998 | Branam | |
| 5,816,799 A | 10/1998 | Parker | |
| 5,876,199 A | 3/1999 | Bergersen | |
| 5,882,192 A | 3/1999 | Bergersen | |
| 5,911,576 A | 6/1999 | Ulrich et al. | |
| 5,975,893 A * | 11/1999 | Chishti et al. | 433/6 |
| 6,129,084 A | 10/2000 | Bergersen | |
| 6,183,248 B1 * | 2/2001 | Chishti et al. | 433/6 |
| 6,299,440 B1 | 10/2001 | Phan et al. | |
| 6,302,686 B1 * | 10/2001 | Chott et al. | 433/6 |
| 6,454,565 B2 | 9/2002 | Phan et al. | |
| 6,505,625 B1 | 1/2003 | Uenishi | |
| 2002/0187451 A1 * | 12/2002 | Phan et al. | 433/6 |
| 2003/0186184 A1 * | 10/2003 | Chishti et al. | 433/6 |

OTHER PUBLICATIONS

Warunek et al., "Clinical Use of Silicone Elastomer Appliances", JCO, vol. 23, No. 10, Oct. 1989, pp. 694-700.*

Wells, "Application of the Positioner Appliance in Orthodontic Treatment", American Journal of Othodontics, Oct. 1970.*

International Preliminary Examination Report, WO 98/58596, Dec. 30, 1998.

* cited by examiner

ORTHODONTIC APPLIANCE, A SYSTEM AND A METHOD FOR AUTOMATICALLY STRAIGHTENING TEETH

This application claims the benefit of U.S. Provisional Application Ser. No. 60/383,908, filed May 28, 2002.

BACKGROUND OF THE INVENTION

The present invention generally relates to an apparatus, a system and a method for straightening of teeth. More specifically, the present invention relates to an orthodontic appliance that may be placed on teeth to straighten teeth and a method for using the same.

It is, of course, generally known to provide an apparatus for straightening teeth. Throughout the life of an individual, teeth often require corrective measures to remain healthy or to correct defects with which an individual may be born or develop at later ages, such as an overbite, overjet, crowding, rotations, and/or spacing of teeth. The need for corrective measures for teeth has brought about various procedures, examinations, diagnoses and the like, such as those provided by a dentist or orthodontist, as well as corrective measures in the form of dental appliances which may be worn in the mouth.

However, orthodontists often are inaccessible due to a person's schedule, geographic location or various other reasons. Moreover, such professionals may be unaffordable to some individuals.

Generally, orthodontics is provided during the developmental years of a patient because significant facial growth takes place during this period. Further, during the developmental years, there is typically additional space in the mouth of the patient for easier correction of crowding teeth and for easier straightening of erupting teeth due to the large deciduous molars and relatively smaller permanent premolars that replace them.

It is generally known to provide an appliance made of a material with an elevated durometer or stiffness which is made directly from the exact anatomy of the teeth of a patient. This type of appliance is usually vacuum or pressure formed, often by a machine called "Biostar." (Sold by Dentaurum) The appliance is generally snapped into place into various undercuts. However, it is often difficult to move teeth to their proper position because of the stiffness and relative lack of resiliency of the appliance.

A need, therefore, exists for an improved apparatus and method for providing automatic tooth straightening that may be snapped into place on some teeth that will not need straightening or that will remain in the mouth in a relative constant position without the need for frequent replacement. A need further exists for an improved appliance having a semi-stiff or soft customized part based on the actual anatomy of the teeth of the patient or prefabricated portion based on predicted sizes and shapes of teeth derived from means of groups of teeth for providing tooth straightening for teeth that are erupting. Additionally, a need exists for an improved appliance for the guidance of unerupted teeth into the mouth or for easier and faster straightening of already erupted, crowded, rotated or spaced teeth.

SUMMARY OF THE INVENTION

The present invention generally relates to an appliance or apparatus, a system and a method for automatic tooth straightening. More specifically, the present invention provides a customized appliance that may be placed on teeth to straighten teeth and a method for using the same. The apparatus may be constructed of a stiff material and may be customized to fit a particular patient. The stiff material of the appliance may be snapped into place on some teeth that will not need straightening or that will remain in the mouth in a relative constant position. The teeth that require straightening or guidance into the mouth may be straightened or guided by a semi-stiff or soft customized or prefabricated portion of the appliance.

To fabricate an appliance for a specific patient, the size and shape of the teeth that have not fully erupted into the mouth are predicted. Those teeth already fully erupted in the mouth that require straightening may be properly aligned by the computer or manually on a model for the softer material to be formed around them. In an embodiment of the present invention, the original model of the mouth of a patient is laser scanned. A computer program to estimate the size and shape of the predicted teeth based on the size of the original existing teeth of the patient and the shape based on group standards or means is provided. The actual cast of the original teeth and predicted teeth may be manually made, or a digital three-dimensional image of the same, may be used to construct a model by stereolithography used in tool and die work, from which an appliance, or several graduated appliances, may be manually fabricated. The appliance or several graduated appliances may also be fabricated by stereolithography directly from the digital three-dimensional model.

To this end, in an embodiment of the present invention, a generally U-shaped orthodontic appliance worn on teeth in a mouth of a patient wherein at least one of the teeth require correcting and further wherein the orthodontic appliance has a plurality of layers of material is provided. The orthodontic appliance has a first layer constructed from a first material. The orthodontic appliance has a second layer adjacent to the first layer constructed from a second material wherein the second material is harder than the first material. The orthodontic appliance also has a first socket formed within the first layer wherein the socket causes movement of a position of at least one of the tooth.

In an embodiment, the orthodontic appliance has a second socket formed within the first layer wherein the second socket maintains the position of at least one of the tooth.

In an embodiment, the orthodontic appliance has walls extending from the first layer.

In an embodiment, the first socket is shaped to correspond to at least one of the teeth.

In an embodiment, the orthodontic appliance has walls extending from the second layer.

In another embodiment of the present invention, a method for correcting a position of a tooth in a mouth of a patient having teeth wherein one of the teeth has a correct position and one of the teeth has an incorrect position is provided. The patient also has a plurality of types of teeth wherein one of the types of the teeth is erupted teeth. The method has the steps of: identifying the position of the tooth; creating an image from the position of the tooth; and predicting a size of an unerupted tooth based on a size of an erupted tooth of the patient.

In an embodiment, the method further has the step of determining the correct position of one of the teeth having the incorrect position based on a model of the tooth wherein the model represents the correct position of the tooth.

In an embodiment, the method further has the step of fabricating an appliance based on the correct position of the tooth.

In an embodiment, the method further has the step of creating a dental appliance having a first portion which contacts a first tooth having the incorrect position wherein the first portion is shaped based on the correct position of the tooth and wherein the dental appliance has a second portion which contacts a second tooth having a correct position.

In an embodiment, the method further has the step of scanning the teeth of the patient to create the image of the position of the tooth.

In an embodiment, the method further has the step of photographing the teeth of the patient to create the image of the position of the tooth.

In an embodiment, the method further has the step of radio-graphing the teeth of the patient to create the image of the position of the tooth.

In an embodiment, the method further has the step of basing the prediction of the size of the unerupted tooth on race-based anatomical standards for teeth.

In an embodiment, the method further has the step of basing the prediction of the size of the unerupted tooth on mesio-distal standards for teeth.

In an embodiment, the method further has the step of predicting a shape of the unerupted tooth based on standard shapes for teeth.

In another embodiment of the present invention, an orthodontic appliance for teeth of a patient having either a correct position or an incorrect position in the mouth of the patient is provided. The orthodontic appliance has a base sized to fit the teeth of the patient. The orthodontic appliance also has a first slot in the base having a first occlusal surface wherein the first slot is constructed from a first material. The orthodontic appliance also has a second slot in the base having a second occlusal surface wherein the second slot is constructed from a second material and further wherein the first material is harder than the second material and wherein the second slot guides one of the teeth having the incorrect position into the correct position.

In an embodiment, the orthodontic appliance has a socket within the base wherein the socket is shaped in correlation to individual teeth of the user.

In an embodiment, the orthodontic appliance has a socket within the base wherein the socket is sized to receive two or more teeth of the user.

In an embodiment, the first material is adjacent to teeth to be maintained.

In an embodiment, the second material is adjacent to teeth requiring correction.

In an embodiment, the occlusal surface is flat.

In another embodiment of the present invention, a method for adjusting teeth of a patient is provided. The method has the steps of: identifying an orthodontic condition of the teeth of the patient; estimating a position of the teeth wherein the position is a correct position in the mouth of the patient and further wherein the correct position provides a proper occlusion of the teeth of the patient; and creating a dental appliance having a socket to rotate the teeth of the patient into the correct position wherein the socket is based on a predicted size of a tooth which has not erupted.

In an embodiment, the method further has the step of creating a model of the teeth of the patient.

In an embodiment, the method further has the step of providing a second socket in the dental appliance wherein the second socket maintains a position of a tooth having the correct position.

In an embodiment, the method further has the step of obtaining an image of the teeth of the patient.

In an embodiment, the method further has the step of calculating a distance between the position of the tooth and the correct position for the tooth.

In an embodiment, the method further has the step of creating a retainer shaped to receive the teeth of the patient when the teeth are in the correct position.

In another embodiment of the present invention, a system for adjusting teeth of a patient is provided. The system has an image capturing device which obtains an image of the teeth of the patient wherein at least one of the teeth has an incorrect position. The system also has a central processing unit which receives the image of the teeth from the image capturing device wherein the central processing unit estimates a correct position of the teeth and further wherein the central processing unit determines a shape of a first dental appliance worn adjacent to the teeth based on the correct position of the tooth.

In an embodiment, the central processing unit determines a shape of a second dental appliance worn adjacent to the teeth after the first dental appliance is worn wherein the second dental appliance maintains the tooth in the correct position.

In another embodiment of the present invention, a generally U-shaped orthodontic appliance for teeth of a patient having either a correct position or an incorrect position in the mouth of the patient wherein a predicted position is a correction of the incorrect position in the mouth is provided. The orthodontic appliance has a base sized to fit the teeth of the patient wherein the base is constructed from a single material. The orthodontic appliance also has a first socket in the base to receive one of the teeth in the incorrect position and further wherein the first socket causes movement of one of the teeth in the incorrect position to the predicted position.

In an embodiment, the orthodontic appliance has a second socket in the base to receive one of the teeth in the correct position.

In an embodiment, the first socket is shaped to correspond to a plurality of the teeth in the incorrect position.

It is, therefore, an advantage of the present invention to provide an apparatus, a system and a method for automatic straightening of teeth with fewer appliances, fewer or no adjustments and fewer or no appointments.

Another advantage of the present invention is to provide an apparatus, a system and a method for straightening of teeth that is simple to use.

Yet another advantage of the present invention is to provide an apparatus, a system and a method for straightening of teeth that requires little or no adjustments by a dentist or orthodontist.

Further, an advantage of the present invention is to provide an apparatus, a system and a method for straightening of teeth wherein the apparatus may be constructed of stiff material, soft resilient material, or a combination of both stiff and soft resilient material.

Another advantage of the present invention is to provide an apparatus, a system and a method for straightening teeth that may be less costly than conventional methods.

A still further advantage of the present invention is to provide an apparatus, a system and a method for straightening of teeth wherein teeth of a patient may be duplicated and straightened by a computer or manually.

Yet another advantage of the present invention is to provide an apparatus, a system and a method for straightening of teeth wherein the apparatus may be fabricated by computer using stereolithography or manually.

Another advantage of the present invention is to provide an apparatus, a system and a method for straightening teeth, guiding erupting teeth and guiding the eruption of yet unerupted teeth, wherein the prediction of the sizes and shapes of certain teeth to be adjusted or guided in eruption may be based on the sizes and shapes of other adult teeth already fully erupted in the mouth of the patient or from group standards.

Further, an advantage of the present invention is to provide an apparatus, a system and a method for straightening of teeth wherein the apparatus may require few or no adjustments or appointments.

Still further, another advantage of the present invention may be to provide an apparatus, a system and a method for straightening of teeth providing a computer generated three-dimensional digital model or image of the dentition.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
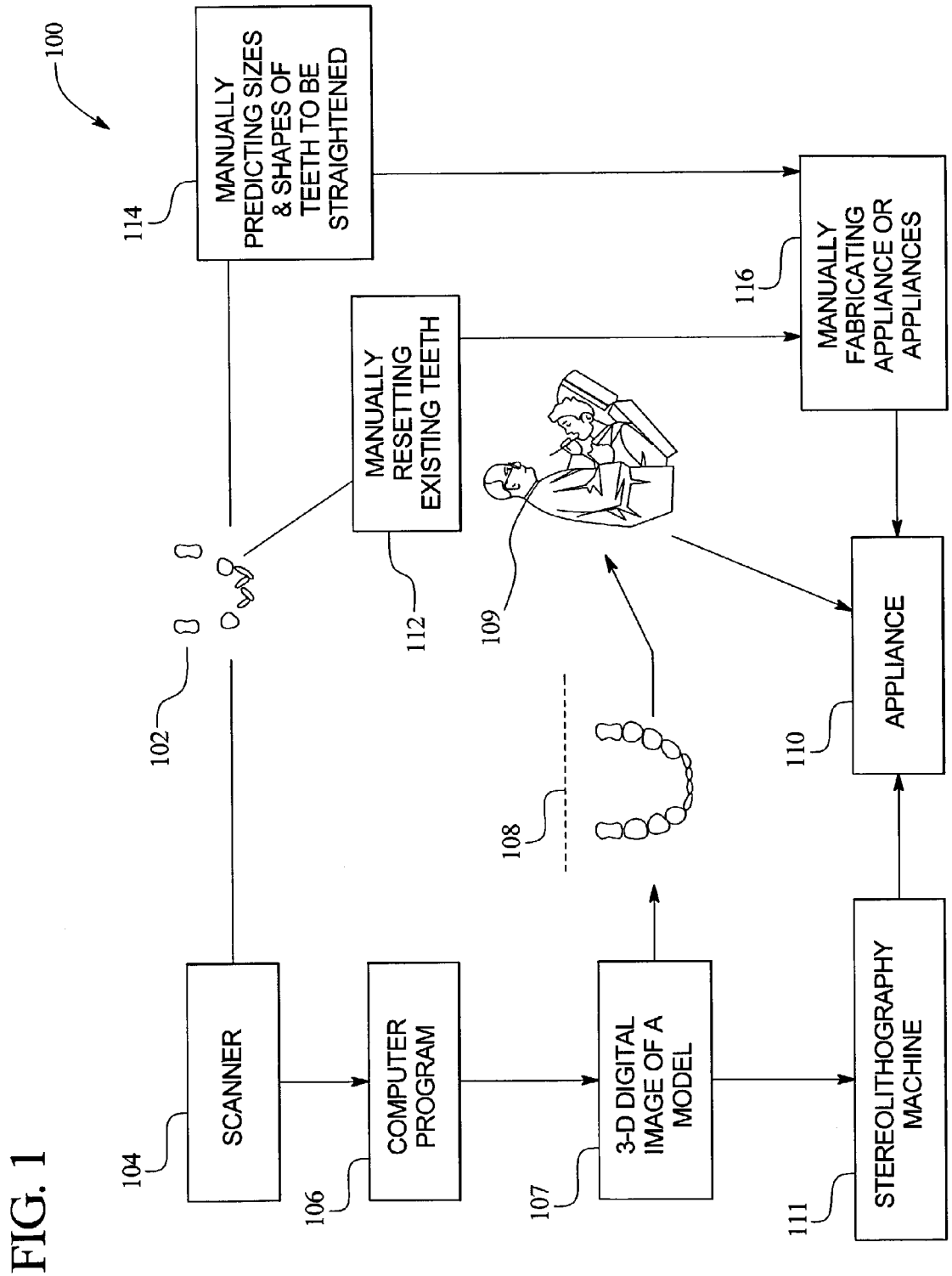
FIG. 1 illustrates a black box diagram of a system in an embodiment of the present invention.

The present invention generally relates to an apparatus, a system and a method for automatic tooth straightening. More specifically, the present invention provides an appliance that may be placed on teeth to straighten teeth and provides a system and method for using the same. The apparatus may be customized to fit a particular patient wherein a portion of the appliance may be attached to erupted teeth that are substantially straight. (Erupted teeth are teeth that have substantially emerged through the gum of the mouth into full biting relation with the opposite arch or jaw.) The appliance may remain in the mouth in a relative constant position. The erupted teeth that require straightening may be straightened; and the unerupted teeth or the teeth that are erupting may be guided into the mouth by another portion of the appliance.

To fabricate an apparatus such that the apparatus has a substantially similar anatomy as that of a mouth of a patient, the size and shape of the teeth that have not fully erupted or not yet exited the gums into the mouth may be predicted. The predictions may be accomplished by analyzing sizes of some of the fully erupted adult teeth and shapes from group standards of tooth shapes. From analyzing the sizes of the fully erupted adult teeth, the size of the unerupted or erupting teeth may be calculated as shown in the table below. The shapes of the erupting or non-erupted teeth may be obtained from standards of average anatomic shapes of groups of teeth.

| Predicting mesio-distal sizes of adult teeth | | | |
|---|---|---|---|
| Lateral (lower) = | Central (lower) | + | 0.5 mm |
| Central (upper) = | Central (lower) | + | 3.25 mm |
| Lateral (upper) = | Central (upper) | + | 2.0 mm |
| Lateral (upper) = | Central (lower) | + | 1.25 mm |
| Incisors (lower 4) = | Central (lower) × 4 | + | 1.0 mm |
| Incisors (upper 4) = | Incisors (lower 4) | + | 8.0 mm |
| Canine (upper) = | Lateral (upper) | + | 1.25 mm |
| Canine (upper) = | Central (upper) | − | 1.0 mm |
| Canine (upper) = | Canine (lower) | + | 1.0 mm |
| Premolar = (upper 1$^{st}$ or 2nd) | Central (upper) | − | 1.8 mm |
| Canine (lower) = | Central (lower) | + | 1.5 mm |
| 1$^{st}$ Premolar (lower) = | Central (lower) | + | 1.6 mm |
| 2$^{nd}$ Prmolar (lower) = | Central (lower) | + | 1.9 mm |
| 2$^{nd}$ Permanent = Premolar (upper) | Dec. 2$^{nd}$ molar (upper) | − | 2.25 mm (approx) |
| 2$^{nd}$ Permanent = Premolar (lower) | Dec. 2$^{nd}$ molar (lower) | − | 2.6 mm (approx) |
| Leeway space lower per side = (canine, both premolars) | | | 2.5 mm* |
| Leeway space upper per side = (canine, both premolars) | | | 1.4 mm* |
| Low. dec. canine & molars per side (male) = | | | 23.55 mm |
| Low. perm. canine & premolars per side = | | | 21.32 mm |
| Difference per side = 2.23 mm. MALE | | | |
| Low. dec. canine & molars per side (female) = | | | 23.03 mm |
| Low. perm. canine & premolars per side = | | | 20.36 mm |
| Difference per side = 2.67 mm. FEMALE | | | |
| Mean difference lower (male & female per side = 2.5 mm | | | |
| Upp. dec. canine & molars per side (male) = | | | 23.08 mm |
| Upp. perm. canine & premolars per side = | | | 21.78 mm |
| Difference per side = 130 mm MALE | | | |
| Upp. dec. canine & molars per side (female) = | | | 22.46 mm |
| Upp. perm. canine & premolars per side = | | | 21.00 mm |
| Difference per side = 1.46 mm. FEMALE | | | |
| Mean difference upper (male & female per side) = 1.4 mm | | | |

*Average of Male and Female
(See Moorrees, C. F. A.: *The Dentition of the Growing Child*, Harvard University Press, Cambridge, Mass, 1959.)

The average size and shape of each tooth not fully erupted in the mouth and corresponding to the various sizes of other teeth in the mouth may be estimated from a computer program. The other teeth in the mouth may also be estimated manually using charts and various altered models of teeth.

Referring to FIG. 1, a black box diagram of a system for straightening teeth 100 is provided. An original model of the mouth of a patient 102 with crowded incisor teeth and unerupted premolars may be scanned by a laser scanner 104. The scanned information may be used to construct a resin model 108 by stereolithography with straightened incisors and predicted fully-erupted premolars in place with the first permanent molars adjusted forward through the leeway space. Additionally, graduated models may be constructed in order to fabricate appliances to be constructed in a graduated series with gradual changes to allow the teeth to move sequentially from the initial actual or digital model to the final model. A person 109 may manually fabricate an appliance with use of the resin model to form a single appliance 110 for straightening teeth. Additionally, the appliance 110 may be modified and fabricated by stereolithography 111 directly from the computer program 106 that provides a three-dimensional digital image of a model 107. The original model 102 may also be manually made by again resetting the teeth required to be straightened 112, or manually predicting sizes and shapes of teeth to be straightened or that are erupting 114. An appliance or appliances may be manually fabricated from these models 116.

Figure 2:
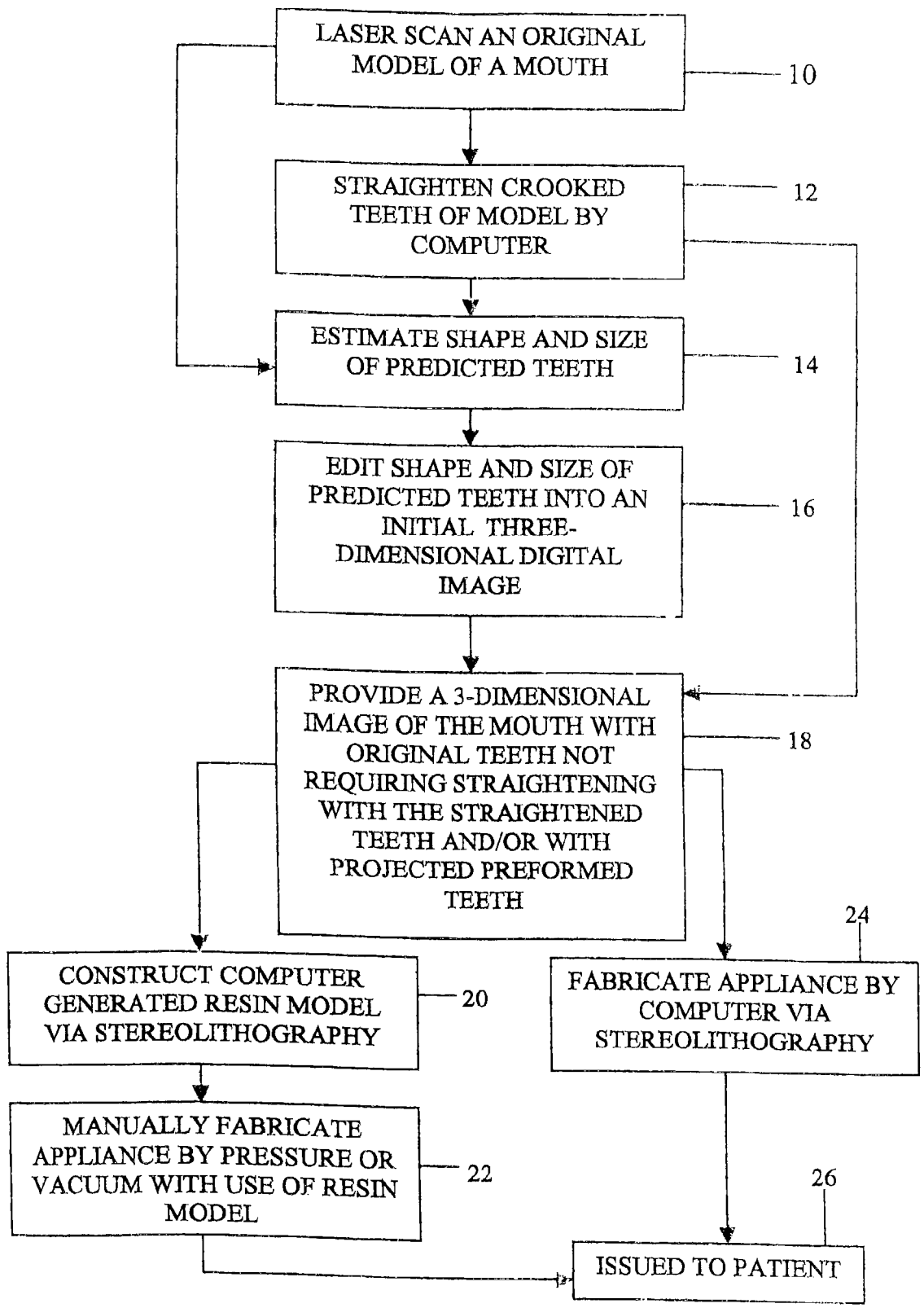
FIG. 2 illustrates a flowchart of a method in an embodiment of the system of the present invention.

More specifically, referring to FIG. 2, a flowchart of a method for forming a model of a mouth for an apparatus to straighten the teeth of that mouth is provided. First, the original model of a mouth of a patient may be laser-scanned via step 10. Laser-scanning a model of a mouth of a patient is known in the art and is disclosed in U.S. Pat. No. 5,975,893 to Chishli et al. After laser-scanning the model, the existing maloccluded or crooked teeth are straightened by computer via step 12 and/or the shape and the size of the predicted teeth may be estimated by a computer via step 14 and may be edited into an initial digital image via step 16. The initial digital image may provide a total digital three-dimensional image and/or cast of the mouth with the original existing straightened teeth together with the projected prefabricated teeth via step 18. Next, either a generated plastic appliance may be computer fabricated by stereolithography via step 24 consisting of predicted preformed teeth and/or actual straightened teeth, or a computer generated resin model via step 20 consisting of similar preformed and/or actual teeth may be made again by stereolithography. This model may then be used to construct thermoplastic, thermosetting plastic or rubber appliances.

The computer-generated stereolithography fabricated resin cast or model of predicted and/or straightened actual teeth may be used to fabricate a single appliance or several graduated appliances may be fabricated manually by pressure or a vacuum with use of graduated resin models via step 22. Alternatively, the appliance or graduated appliances may be fabricated directly by the computer via a stereolithography technique similarly used in tool and die work as shown at step 24 which can bypass the necessity of making a single or graduated resin models. The appliance or appliances may then be issued to the patient via step 26. The computer program may combine a virtual three-dimensional partial digital model with a partial three-dimensional digital prefabricated model of predicted teeth to form a single appliance or multiple appliances or resin model or graduated models from which appliances can be constructed. The computer generated or manually fabricated appliances may be constructed of a total stiff and/or a semi-stiff or soft material or a combination of both, such as, for example, plastic, rubber, or other material with similar properties.

Figure 4:
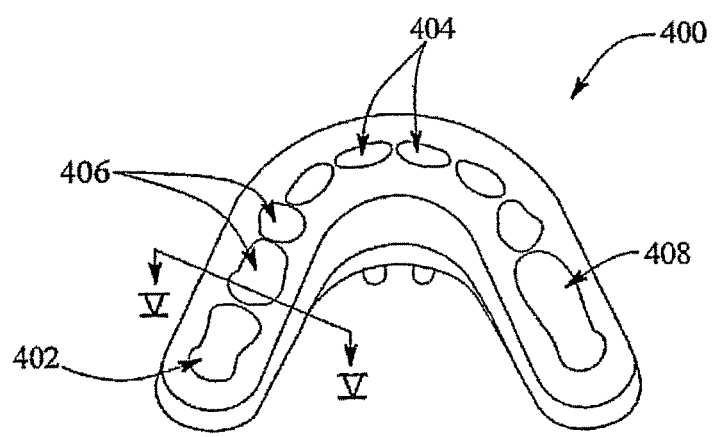
FIG. 4 illustrates a perspective view of an appliance in an embodiment of the present invention.

In an embodiment, an initial model of the teeth of a patient may be made from a manual model of the mouth of a patient. The initial model of the teeth of the patient may also be fabricated by digital photography from various angles of the mouth, digital radiographs or other similar imaging devices. The imaging devices may be combined with an estimate of sizes and/or shapes of various erupting teeth or future eruption of teeth not yet through tissue in various areas of the mouth or including an estimate of sizes and shapes of similar unerupted teeth or slots 408 (as shown in FIG. 4) for more than one tooth. Single or multiple appliances may be fabricated from a stiff plastic or a soft resilient plastic or a combination of both stiff and soft plastic or other material with similar properties.

Figure 3:
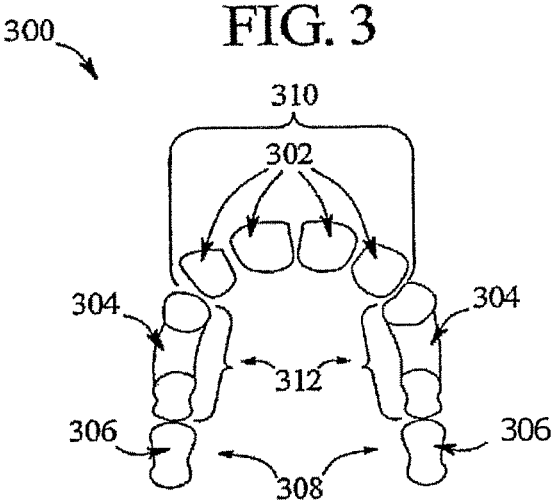
FIG. 3 illustrates a top view of a mouth used to form a model in an embodiment of the present invention.

Referring now to FIG. 3, a mouth 300 of a patient with teeth 302 that may require straightening, sockets 304 for new or missing teeth, and permanent or deciduous substantially straight teeth 306 are generally illustrated. An appliance (not shown) for straightening the teeth may be constructed from, for example, rubber or plastic or other material known by those skilled in the art. The appliance or appliances may correct orthodontic conditions such as overbite, overjet and the like and may be worn in the mouth of a user. The appliance may have many different configurations to correct an orthodontic condition, depending on the age and number of deciduous and adult teeth present in the mouth of the user and for those teeth not yet erupted into the mouth but anticipated to be guided into position.

FIG. 3 further illustrates a first area 308 in the mouth 300 to be cast in a stiff material and a second area 310 in the mouth 300 to be cast in soft resilient material. FIG. 3 further illustrates a prefabricated area 312 for the unerupted permanent teeth of a patient that will be erupting into the mouth in the near future.

Referring to FIG. 4, an appliance 400 of the present invention is generally illustrated. The appliance 400 may have a first area 402 constructed of a stiff material for attachment to substantially straight erupted teeth. The appliance may further have a second area 404 constructed of a soft resilient material for guiding unerupted teeth into the mouth of adult teeth or teeth that require straightening and a third area 406 for straightening either maloccluded teeth in the mouth or to guide unerupted adult teeth into the mouth into prefabricated sockets or prefabricated slots or grooves for one or more teeth. This area may also be beneficial if made of a soft resilient material. Further, it may be possible to have stiff material extended forward as an outer or interior supporting structure with softer material inside the appliance and contacting the teeth or around the entire outer surface of the appliance. The inner (lingual) walls with softer material contact the teeth surfaces within the same arch, while the outer (buccal, labial and occlusal) surfaces contact the cheeks and teeth surfaces in the same and/or opposite arch.

Figure 5A:
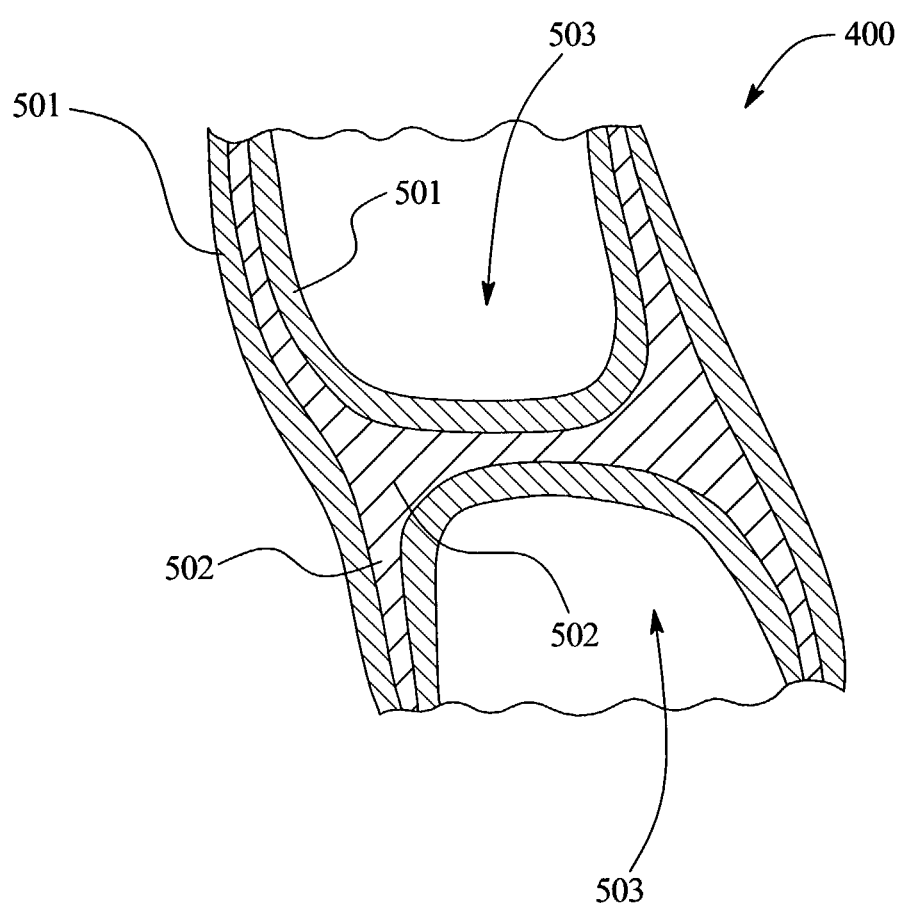
FIG. 5A illustrates a cross sectional view taken along line V-V of FIG. 4 of an embodiment of the present invention having a stiffer section where the teeth do not require straightening, and a softer section in an area where the teeth require straightening which is in direct contact with the teeth.
Figure 5B:
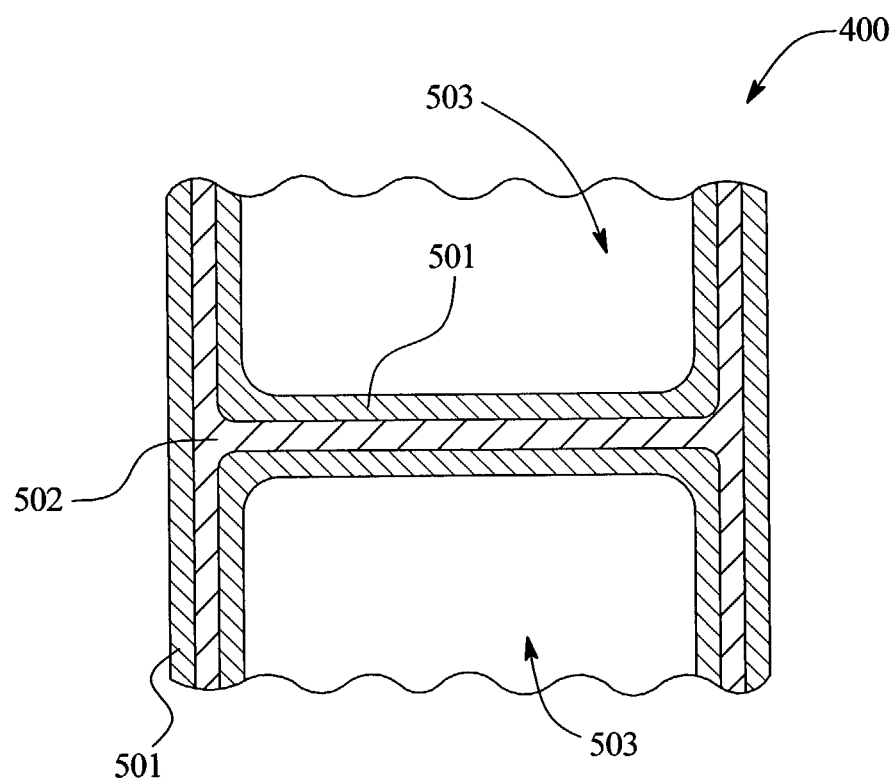
FIG. 5B illustrates a cross sectional view of the appliance in another embodiment of the present invention.
Figure 5C:
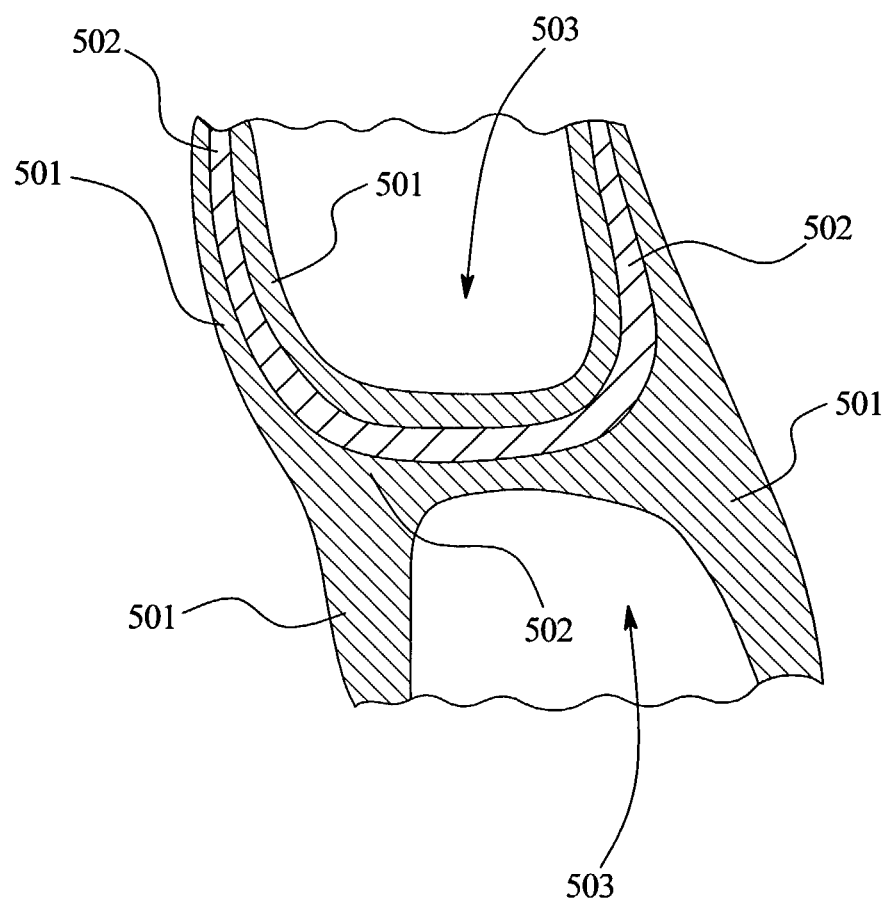
FIG. 5C illustrates a cross sectional view of the appliance in another embodiment of the present invention.

Referring to FIGS. 5A, 5B, and 5C, cross sectional views in different embodiments of the appliance are generally illustrated. The appliance may have a stiffer section where the teeth do not require straightening, and a softer section in an area where the teeth require straightening which is in direct contact with the teeth. The third area 406 (shown in FIG. 4) or any other area of the appliance 400 may have a soft outer layer 501. The soft outer layer 501 may be made of a resilient material. Within the soft outer layer 501 may be a stiff inner layer 502. The stiff inner layer 502 of the appliance 400 may provide support for the appliance 400. Further, within the third area 406 of the appliance 400 may be a preformed socket 503. The preformed socket 503 may be predicted from the size of other existing adult teeth in the mouth while the shape is predicted from standards of many other similar teeth. Additionally, the socket 503 may be a custom fabricated socket duplicated from the same existing fully erupted adult or deciduous teeth in the mouth.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A dental appliance worn on teeth of a patient wherein the teeth of the patient form a dentition, the dental appliance comprising:

a generally U-shaped base having an upper face and a lower face wherein the upper face is opposite to the lower face wherein the base has an interior made of a first material wherein the interior has a generally H-shaped cross-section and an exterior formed around the interior wherein the upper face is sized to receive one or more teeth of the patient therein wherein the lower face is sized to receive one or more teeth of the patient therein wherein the exterior is made of a second material wherein the exterior of the base encloses the interior of the base and further wherein the first material is harder than the second material during use by the patient under ambient conditions.

2. The dental appliance of claim 1 wherein the base automatically straightens the teeth of the patent.

3. The dental appliance of claim 1 further comprising:
a socket within the base.

4. The dental appliance of claim 1 further comprising:
an occlusal surface on the base.

5. A dental appliance for teeth of a patient, the dental appliance comprising:
a generally U-shaped base having an upper face and a lower face wherein the upper face is opposite to the lower face; and
sockets within the upper face and the lower face wherein at least one of the sockets receives one or more teeth of the patient therein wherein at least one of the sockets has an exterior made of a first material and an interior made of a second material wherein the interior has a generally H-shaped cross-section wherein the exterior is formed around the interior wherein the first material is softer than the second material and further wherein the exterior of at least one of the sockets encloses the interior of at least one of the sockets.

6. The dental appliance of claim 5 wherein the base automatically straightens the teeth of the patient.

7. The dental appliance of claim 5 wherein the sockets are based on standard shapes and standard sizes for teeth.

8. The dental appliance of claim 5 wherein the sockets are duplications of the teeth of the patient.

9. An orthodontic appliance for teeth of a patient having either a correct position or an incorrect position in the mouth of the patient, the appliance comprising:
a base having an upper face and a lower face wherein the upper face is opposite to the lower face wherein the base has an interior layer constructed from a first material wherein the interior layer has a generally H-shaped cross-section and an exterior layer formed around the interior layer wherein the exterior layer encloses the interior layer wherein the exterior layer is constructed from a second material wherein the second material is harder than the first material; and
a slot formed in the upper face or the lower face having an occlusal surface wherein the slot is configured to receive a plurality of teeth of the patient therein wherein the slot guides one of the teeth having the incorrect position into the correct position and further wherein the base attaches to one or more teeth of the patient via the exterior layer of the base.

10. The appliance of claim 9 further comprising:
a socket formed in the base wherein the socket is shaped in correlation to individual teeth of the patient.

11. The appliance of claim 9 further comprising:
a socket formed in the base wherein the socket is sized to receive one or more teeth of the patient therein.

12. The appliance of claim 9 wherein the second material is adjacent to teeth to be maintained.

13. The appliance of claim 9 wherein the second material is adjacent to teeth requiring correction.

14. The appliance of claim 9 wherein the occlusal surface is flat.

15. A dental appliance worn on teeth in a mouth of a patient wherein at least one of the teeth require correction, the dental appliance comprising:
a base having an upper face and a lower face wherein the upper face is opposite to the lower face wherein the upper face is sized to receive one or more teeth of the patient wherein the lower face is sized to receive one or more teeth of the patient wherein the base has an interior layer constructed from a first material wherein the interior layer has a generally H-shaped cross-section and an exterior layer formed around the interior layer wherein the exterior layer encloses the interior layer wherein the exterior layer is constructed from a second material wherein the second material is harder than the first material; and
a socket formed in the exterior layer of the upper face or the lower face wherein the socket is sized to receive one or more teeth of the patient therein wherein the exterior layer of the base contacts the teeth to move one or more of the teeth to a correct position wherein the base is attached to one or more teeth of the patient via the exterior layer of the base.

16. The dental appliance of claim 15 further comprising:
a slot formed in the base wherein the slot is shaped to receive one or more teeth of the patient therein.

17. The dental appliance of claim 15 wherein the socket is preformed based on anatomical standard shapes and sizes of teeth.

18. The dental appliance of claim 15 wherein the socket is shaped based on a predicted shape of one of the teeth of the patient which have not erupted.

19. The dental appliance of claim 15 wherein the socket is shaped to correspond to a shape of one of the teeth.

20. The dental appliance of claim 15 further comprising:
an occlusal area formed in the exterior layer of the base wherein the occlusal area is customized based on one or more teeth of the patient wherein the occlusal area contacts one or more teeth of the patient.

21. The dental appliance of claim 15 further comprising:
an occlusal area formed in the exterior layer of the base wherein the occlusal area is preformed and customized based on one or more teeth of the patient wherein the occlusal area contacts one or more teeth of the patient.

22. A generally U-shaped orthodontic appliance worn on teeth in a mouth of a patient wherein at least one of the teeth require correcting and further wherein the orthodontic appliance has a plurality of layers of material, the orthodontic appliance comprising:
a base having an upper face and a lower face wherein the upper face is opposite to the lower face wherein the base has an interior layer constructed from a first material wherein the interior layer has a generally H-shaped cross-section and an exterior layer formed around the interior layer wherein the exterior layer encloses the interior layer wherein the exterior layer is constructed from a second material wherein the first material is harder than the second material;
a socket formed within the exterior layer of the upper face and the lower face wherein the socket is sized to receive one or more teeth of the patient therein wherein the exterior layer surrounds at least one of the teeth of the patient wherein the socket causes movement of a position of at least one of the teeth; and
walls extending from the exterior layer.

23. A generally U-shaped orthodontic appliance worn on teeth in a mouth of a patient wherein at least one of the teeth require correcting and further wherein the orthodontic appliance has a plurality of layers of material, the orthodontic appliance comprising:
a base having an upper face and a lower face wherein the upper face is opposite to the lower face wherein the base has an interior layer constructed from a first material wherein the interior layer has a generally H-shaped cross-section and an exterior layer formed around the interior layer wherein the exterior layer encloses the interior layer wherein the exterior layer is constructed from a second material wherein the first material is harder than the second material;
a socket formed within the exterior layer of the upper face and the lower face wherein the socket is sized to receive one or more teeth of the patient therein wherein the exterior layer surrounds at least one of the teeth of the patient wherein the socket causes movement of a position of at least one of the teeth; and
walls extending from the interior layer.

24. A dental appliance worn on teeth of a patient wherein the teeth of the patient form a dentition, the dental appliance comprising:
a generally U-shaped base sized to fit the teeth of the patient;
first sockets within the base wherein the first sockets are customized to receive one or more teeth of the patient; and
second sockets within the base wherein the second sockets are predicted based on corrected positions of one or more teeth of the dentition of the patient wherein the second sockets are formed to receive one or more teeth of the patient wherein the first sockets or the second sockets accommodate the dentition of the patient wherein the dentition of the patient has deciduous erupted teeth, permanent erupted teeth or unerupted teeth wherein the second sockets are based on standard shapes and standard sizes for teeth.

25. A dental appliance worn on teeth of a patient, the dental appliance comprising:
a generally U-shaped a base having an upper face and a lower face wherein the upper face is opposite to the lower face; and
sockets within the upper face and the lower face wherein at least one of the sockets receives one or more teeth of the patient therein wherein at least one of the sockets has an exterior made of a first material wherein the exterior is formed around an interior made of a second material wherein the second material is harder than the first material wherein the interior has a generally H-shaped cross-section and further wherein the exterior of at least one of the sockets encloses the interior of at least one of the sockets.

26. The dental appliance of claim 25 wherein the sockets are based on standard shapes and standard sizes for teeth.

27. A dental appliance worn on teeth in a mouth of a patient wherein at least one of the teeth require correction, the dental appliance comprising:
a base sized to fit the teeth of the patient wherein the base has an interior layer constructed from a first material wherein the interior layer has a generally H-shaped cross-section and an exterior layer formed around the interior layer wherein the exterior layer encloses the interior layer wherein the exterior layer is constructed from a second material wherein the first material is harder than the second material; and
a socket formed in the exterior layer of the base wherein the socket is sized to receive one or more teeth of the patient therein wherein the exterior layer of the base contacts the teeth to move one or more of the teeth to a correct position wherein the base is attached to one or more teeth of the patient via the exterior layer of the base wherein the socket is shaped based on a predicted shape of one of the teeth of the patient which have not erupted.

* * * * *